(12) United States Patent
Rahafrooz et al.

(10) Patent No.: US 9,571,013 B2
(45) Date of Patent: Feb. 14, 2017

(54) MICROMECHANICAL RESONATORS

(75) Inventors: Amir Rahafrooz, Denver, CO (US);
Arash Hajjam, Denver, CO (US);
Siavash Pourkamali, Aurora, CO (US)

(73) Assignee: COLORADO SEMINARY, Denver, CO (US)

(*) Notice: Subject to any disclaimer, the term of this patent is extended or adjusted under 35 U.S.C. 154(b) by 199 days.

(21) Appl. No.: 13/878,980

(22) PCT Filed: Oct. 12, 2011

(86) PCT No.: PCT/US2011/055911
§ 371 (c)(1),
(2), (4) Date: Jul. 17, 2013

(87) PCT Pub. No.: WO2012/051256
PCT Pub. Date: Apr. 19, 2012

(65) Prior Publication Data
US 2013/0285676 A1  Oct. 31, 2013

Related U.S. Application Data

(60) Provisional application No. 61/392,354, filed on Oct. 12, 2010.

(51) Int. Cl.
*H03H 9/24* (2006.01)
*H02N 11/00* (2006.01)
*H03H 3/007* (2006.01)
*H03H 9/02* (2006.01)
*G01N 22/00* (2006.01)
*G01N 15/10* (2006.01)

(52) U.S. Cl.
CPC ............ *H02N 11/006* (2013.01); *G01N 15/10* (2013.01); *G01N 22/00* (2013.01); *H03H 3/0072* (2013.01); *H03H 9/02259* (2013.01); *H03H 9/02448* (2013.01); *H03H 9/2436* (2013.01); *H03H 9/2463* (2013.01); *G01N 2015/1087* (2013.01); *H03H 2009/0233* (2013.01); *H03H 2009/02283* (2013.01)

(58) Field of Classification Search
CPC .......... H03H 2009/02496; H03H 2009/02511; H03H 9/02448; H03H 3/0072; H03H 9/2405; H03H 9/2463
See application file for complete search history.

(56) References Cited

U.S. PATENT DOCUMENTS 3,488,530 A * 1/1970 Staudte .................. 310/348
5,020,370 A   6/1991 Deval et al.
(Continued)

OTHER PUBLICATIONS

International Search Report and Written Opinion of PCT/US2011/055911 mailed on Mar. 23, 2012, 14 pages.

*Primary Examiner* — Alesa Allgood
(74) *Attorney, Agent, or Firm* — Maschoff Brennan

(57) ABSTRACT

Embodiments of the invention include micromechanical resonators. These resonators can be fabricated from thin silicon layers. Both rotational and translational resonators are disclosed. Translational resonators can include two plates coupled by two resonate beams. A stable DC bias current can be applied across the two beams that causes the plates to resonate. In other embodiments, disk resonators can be used in a rotational mode. Other embodiments of the invention include using resonators as timing references, frequency sources, particle mass sensors, etc.

18 Claims, 19 Drawing Sheets

(56) References Cited

U.S. PATENT DOCUMENTS

| | | | |
|---|---|---|---|
| 5,839,062 A * | 11/1998 | Nguyen | H03H 9/02377 332/117 |
| 6,930,569 B2 * | 8/2005 | Hsu | 333/186 |
| 7,586,239 B1 * | 9/2009 | Li et al. | 310/323.02 |
| 2006/0290449 A1 | 12/2006 | Piazza et al. | |
| 2008/0297281 A1 * | 12/2008 | Ayazi et al. | 333/192 |
| 2009/0249873 A1 | 10/2009 | Delevoye | |
| 2011/0025426 A1 * | 2/2011 | Steeneken | H03H 9/02259 331/155 |

\* cited by examiner

| Finite Element Modal Analysis Showing Resonant Mode Shape | Resonator Dimensions (μm) | | | Freq$_{Air}$ (MHz) | Q$_{Air}$ | Freq$_{Hep.}$ (MHz) | Q$_{Hep.}$ |
|---|---|---|---|---|---|---|---|
| | D | L$_{th}$ | H | | | | |
| | 100 | 42 | 5 | 5.500 | 3500 | 5.500 | 145 |
| | | | 10 | 5.144 | 1900 | 5.144 | 175 |
| | | | 20 | 4.052 | 3000 | 4.052 | 215 |
| | | 17 | 5 | 6.827 | 2000 | 6.827 | 155 |
| | | | 10 | 6.427 | 1100 | 6.427 | 180 |
| | | | 20 | 5.356 | 1100 | 5.356 | 180 |
| | 200 | 55.5 | 5 | 2.586 | 4200 | 2.586 | 90 |
| | | | 10 | 2.383 | 700 | 2.383 | 170 |
| | | | 20 | 1.767 | 11700 | 1.767 | 110 |
| | | 35 | 5 | 3.368 | 2800 | 3.368 | 100 |
| | | | 10 | 2.849 | 3000 | 2.849 | 180 |
| | | | 20 | 3.056 | 1400 | 3.056 | 220 |

| Finite Element Modal Analysis Showing Resonant Mode Shape | Resonator Dimensions (μm) | | | Freq$_{Air}$ (MHz) | Q$_{Air}$ | Freq$_{Hep.}$ (MHz) | Q$_{Hep.}$ |
|---|---|---|---|---|---|---|---|
| | D | L$_{th}$ | H | | | | |
| | 100 | 24 | 10 | 7.174 | 3500 | 7.174 | 235 |
| | | | 20 | 4.152 | 3800 | 4.152 | 230 |
| | | 11 | 5 | 7.366 | 1400 | 7.366 | 185 |
| | | | 10 | 8.406 | 600 | 8.406 | 195 |
| | | | 20 | 5.463 | 1700 | 5.463 | 304 |
| | 200 | 40 | 5 | 2.781 | 4900 | 2.781 | 95 |
| | | | 10 | 2.911 | 2600 | 2.911 | 230 |
| | | | 20 | 1.851 | 8500 | 1.851 | 160 |
| | | 24 | 5 | 3.394 | 4000 | 3.394 | 120 |
| | | | 10 | 3.513 | 1100 | 3.513 | 150 |
| | | | 20 | 2.616 | 5500 | 2.616 | 220 |

| Finite Element Modal Analysis Showing Resonant Mode Shape | Resonator Dimensions (μm) | | | Freq_Air (MHz) | Q_Air | Freq_Hep. (MHz) | Q_Hep. |
|---|---|---|---|---|---|---|---|
| | D | L_th | H | | | | |
| | 100 | 114 | 5 | 5.594 | 8000 | 5.594 | 125 |
| | 100 | 114 | 10 | 5.627 | 6500 | 5.627 | 105 |
| | 100 | 114 | 20 | 3.973 | 2000 | 3.973 | 180 |
| | 100 | 103 | 10 | 5.350 | 7800 | 5.350 | 140 |
| | 100 | 103 | 20 | 3.752 | 2300 | 3.752 | 140 |
| | 100 | 42 | 5 | 7.673 | 5000 | 7.673 | 170 |
| | 100 | 42 | 10 | 7.396 | 5000 | 7.396 | 180 |
| | 100 | 42 | 20 | 5.632 | 3200 | 5.632 | 180 |
| | 100 | 84 | 5 | 7.517 | 13500 | 7.517 | 155 |
| | 100 | 84 | 10 | 7.581 | 15000 | 7.581 | 150 |
| | 100 | 84 | 20 | 5.386 | 4800 | 5.386 | 50 |

FIG. 19

MICROMECHANICAL RESONATORS

CROSS REFERENCE

This application is a U.S. National Stage of International Application No. PCT/US2011/055911, filed on Oct. 12, 2011, which claims priority to U.S. Provisional Application No. 61/392,354, filed on Oct. 12, 2010, both of which are incorporated herein by reference in their entireties.

BACKGROUND

Mechanical resonators are widely used in electronic oscillators as highly stable frequency references. In order to realize an electronic oscillator with a mechanical resonator as its frequency reference, the resonator needs to be engaged in a positive feedback loop consisting of amplifying circuitry with the appropriate phase shift. The same requirement applies to the emerging micro-electro-mechanical resonators requiring on-chip or in-package integration of such devices with electronic circuits in order to deliver on the promise of higher levels of integration enabled by MEMS. A variety of MEMS oscillators including both electrostatic and piezoelectric micromechanical resonators and sustaining amplifiers have been demonstrated over the past decade.

BRIEF SUMMARY

Embodiments of the invention include micromechanical resonators. These resonators can be fabricated from thin silicon layers. Both rotational and translational mode resonators are disclosed. Translational resonators can include two plates coupled by two or more actuator beams. A stable DC bias current can be applied across the actuator beams that causes the plates to resonate. In other embodiments, disk resonators can be used in a rotational mode. Other embodiments of the invention include using resonators as timing references, frequency sources, particle mass sensors, chemical or biomedical sensors, etc.

As sensitive mass sensors, micromechanical resonators can potentially open up a wide range of new opportunities in biomedical and chemical sensing applications leading to more compact low cost instruments with real-time sensing capabilities. In addition, due to their small size, micro resonators can be integrated in arrays of hundreds to thousands sensing a variety of analytes simultaneously. Most of the biosensing applications require detection and measurement of certain molecules in a liquid solution.

The terms "invention," "the invention," "this invention" and "the present invention" used in this patent are intended to refer broadly to all of the subject matter of this patent and the patent claims below. Statements containing these terms should not be understood to limit the subject matter described herein or to limit the meaning or scope of the patent claims below. Furthermore, this patent does not seek to describe or limit the subject matter covered by the claims in any particular part, paragraph, statement or drawing of the application. The subject matter should be understood by reference to the entire specification, all drawings and each claim.

BRIEF DESCRIPTION OF THE DRAWINGS

Illustrative embodiments of the present invention are described in detail below with reference to the following figures:

FIG. 19 is a table summarizing measurement results for a resonator having a parallel dual-disk, a resonator having a series dual disk, and a resonator having an interconnected quad-disk.

DETAILED DESCRIPTION

The subject matter of embodiments of the present invention is described with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. Like numerals within the drawings and mentioned herein represent substantially identical structural elements. Each example is provided by way of explanation, and not as a limitation. For instance, features illustrated or described as part of one embodiment may be used on another embodiment to yield a further embodiment. Thus, it is intended that this disclosure includes modifications and variations.

Embodiments of the invention include various micromechanical resonators. Such resonators typically have dimensions less than or equal to about 500 µm. These resonators can have either translational or rotational modes. In some embodiments, two micromechanical plates can be coupled with one or more beams. A constant current can be applied to the resonator through the beams, which starts a cycle of heating and cooling of the beams that result in a corresponding stress and therefore cycle of changes in the resistance of the beams. This change can result in a change in voltage measured across the beams. These cycles can reach resonance producing a constant frequency response with some temperature related drift. Disk resonators can include a disk coupled with two actuating beams. When an actuation current is applied, which may include both a DC and AC component, the disk rotates back and forth with a small amplitude and the beams expand and contract in a manner similar to the beams in translational mode resonators producing regular oscillations.

Resonators

Figure 1:
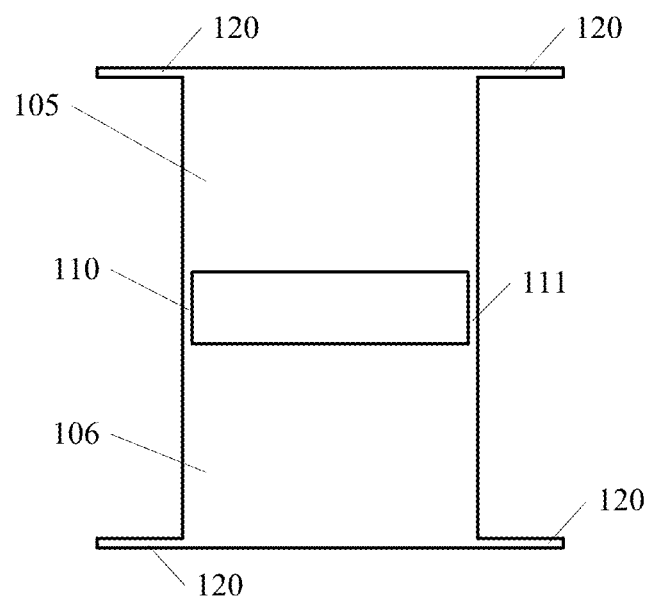
FIG. 1 shows an in-plane resonator according to some embodiments of the invention.

FIG. 1 shows an in-plane resonator according to some embodiments of the invention. Resonator 100 can include plate 105 and plate 106 that are coupled together via beam 110 and beam 111. Resonator 100 can be a monolithic and/or unitary structure. That is, beam 110, beam 111, plate 105, and plate 106 can be constructed from the same material during the same process. In some embodiments, resonator 100 can be etched from a substrate; for example, a substrate with silicon, doped silicon, N-type silicon, P-type silicon, silicon oxide, silicon carbide, germanium, etc. Resonator 100 can be made from any type of conductor or semiconductor material. Resonator 100 can be released from the substrate using any number of undercut methods; for example, using hydrofluoric acid. In some embodiments, beam 110 and/or beam 111 can be thinned down by various post etching techniques such as thermal oxidation and subsequent oxide removal.

Figure 4:
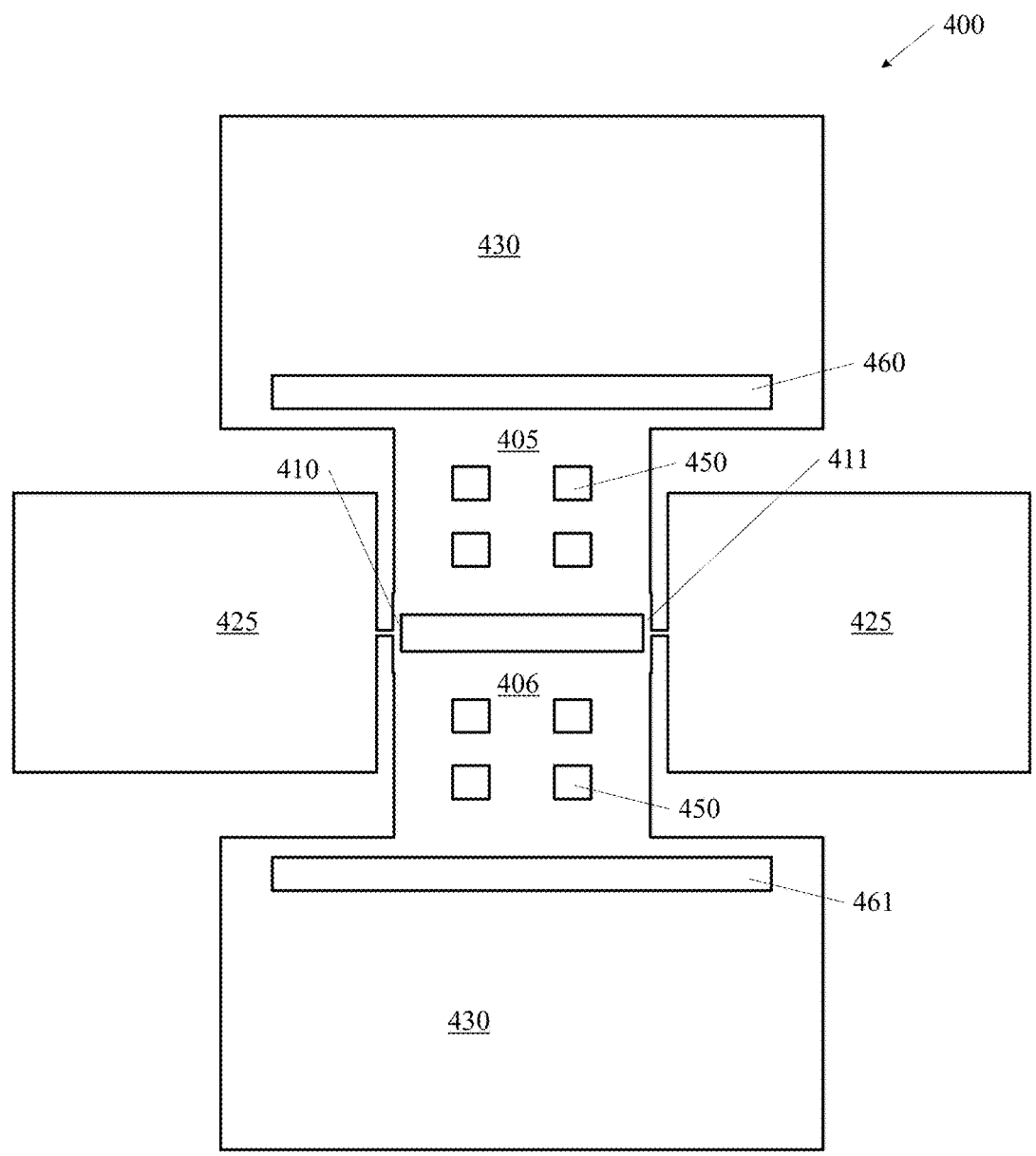
FIG. 4 shows another embodiment of a nano/micromechanical resonator.

Plates 105 and plate 106 can be masses that oscillate relative to one another while beams 110 and 111 expand and contract. That is, plate 105 and plate 106 can move back and forth in opposite directions causing beam 110 and beam 111 to compress and expand periodically when a DC bias current is applied. In some embodiments, the DC bias current can be applied between beam 110 and beam 111, for example, at or near the center of beam 110 and beam 111 (e.g., as shown in FIG. 4). In other embodiments, the DC bias current can be applied between plate 105 and plate 106. Beam 110 and beam 111 can act as thermal actuators and/or piezoresistive sensors.

Support beams 120 on the outer corners of plates 105 and 106 can be included to add vertical stiffness to plates 105 and 106. Support beams 120 may also aide stiction mitigation during undercut and/or release of resonator 100 from a substrate. Support beams 120 can also be used to couple resonator to another structure. In some embodiments, support beams 120 can couple directly with a fixed portion of the substrate from which the resonator is etched.

In some embodiments, the dimensions of beams 110 and 111 are chosen so that their first flexural mode frequency is close to the first in-plane mode of resonator 100. This can be done, for example, in order to minimize acoustic loss through the support beams and/or to maximize resonator mechanical quality factors (Q). In some embodiments, the structures can be aligned to the 100 crystal orientation, where the absolute value of the longitudinal piezoresistive coefficient is maximum. This can be done, for example, to maximize the transduction coefficient of resonator 100.

Plates 105 and 106 can come in various sizes and/or shapes. For example, plates 105 and 106 can be a 10 µm×10 µm square. As one example, plates 105 and 106 can be 5 mm×5 mm square. Plates 105 and 106 can have one, two or three dimensions that are less than 500 µm, 400 µm, 300 µm, 200 µm, 100 µm, 50 µm, 20 µm, 10 µm, 5 µm, 1 µm, 800 nm, 600 nm, 400 nm, 200 nm, 100 nm, etc. Plates 105 and 106 can also be shaped as rectangles, circles, polygons, etc.

In some embodiments, resonator 100 can have a thickness that is less than 100 µm, 80 µm, 60 µm, 40 µm, 20µm, 10 µm, 5 µm, 2 µm, 1 µm, 800 nm, 600 nm, 400 nm, 200 nm, 100 nm, 80 nm, 60 nm, 40 nm, 20 nm, 10 nm, etc. As another example, beams 110 and 111 can have widths less than 20 µm, 10 µm, 5 µm, 4 µm, 2 µm, 1 µm, 800 nm, 600 nm, 400 nm, 200 nm, 100 nm, 80 nm, 60 nm, 40 nm, 20 nm, 10 nm, etc. As yet another example, beams 110 and 111 can be 100 µm, 80 µm, 60 µm, 50 µm, 40 µm, 20µm, 10 µm, 5 µm, 2 µm, 1 µm, 800 nm, 600 nm, 400 nm, 200 nm, 100 nm, 80 nm, 60 nm, 40 nm, 20 nm, 10 nm, etc. long.

Figure 13:
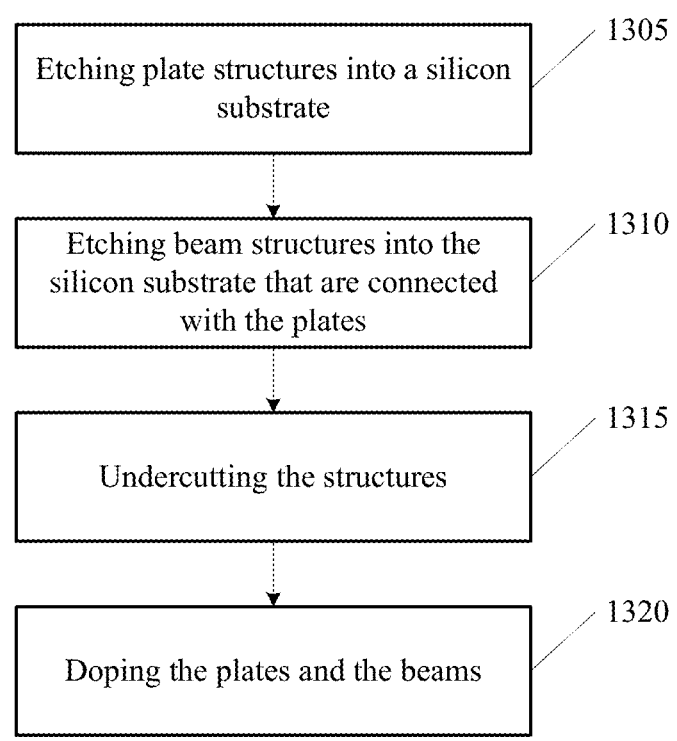
FIG. 13 is a flowchart of a process for fabricating a resonator according to some embodiments of the invention.

Various processes can be used to fabricate resonator 100. FIG. 13 is an example of a flowchart of a process for fabricating a resonator according to some embodiments of the invention. At block 1305 and 1310 the plates and the beams are etched into a substrate. These can be etched in separate steps or in the same step. Pads (e.g., pads 425 shown in FIG. 4) and fixed masses (e.g., anchor 430 shown in FIG. 4) can also be etched into the substrate. Any number of etching or lithography techniques can be used to form the parts of the resonator. For example, wet chemical etching, dry etching, masking, deep reactive ion etching, photolithography, CMOS fabrication processes, etc. techniques can be used At block 1315 the plates and beams can be suspended over the substrate using undercutting techniques. Once etched and possibly undercut, the plates and beams may undergo various post processing steps such as annealing and/or baking These post processing steps may occur before or after undercutting. In some embodiments, the structures may be doped with dopants at block 1320. This doping may occur at any time during the process and may not occur at all.

In some embodiments of the invention, the motional conductance ($g_m$) for resonator 100 can be given by $$g_m = 4\alpha E^2 \pi_l Q \frac{AI_{dc}^2}{KLC_{th}\omega_m}$$

where $\alpha$, $E$, and $\pi_l$ are the thermal expansion coefficient, Young's modulus, and longitudinal piezoresistive coefficient of the structural material that resonator 100 is constructed from. $A$, $L$, and $C_{th}$ are the cross-sectional area, length, and thermal capacitance of beams 110 and 111. $Q$, $K$, $\omega_m$, and $I_{dc}$ are the quality factor, mechanical stiffness, resonance frequency, and bias current of resonator 100. As noted, motional conductance can depend on various physical properties of the resonator.

As opposed to the passive piezoelectric or capacitive micromechanical resonators that typically have a positive (or dissipative) motional resistance, the motional conductance for a thermal-piezoresistive resonator can become negative provided that the structural material has a negative piezoresistive coefficient ($\pi_l$).

Figure 2A:
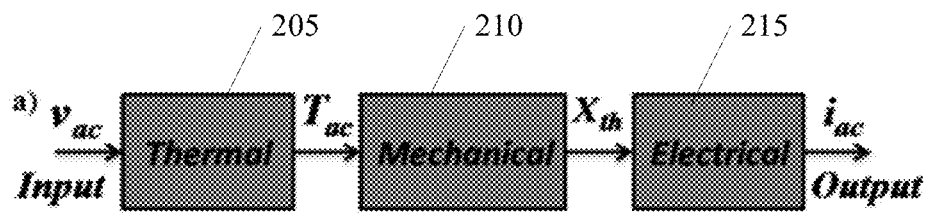
FIG. 2A shows a schematic diagram of the three physical domains involved in operation of thermal-piezoresistive resonators according to some embodiments of the invention.
Figure 2B:
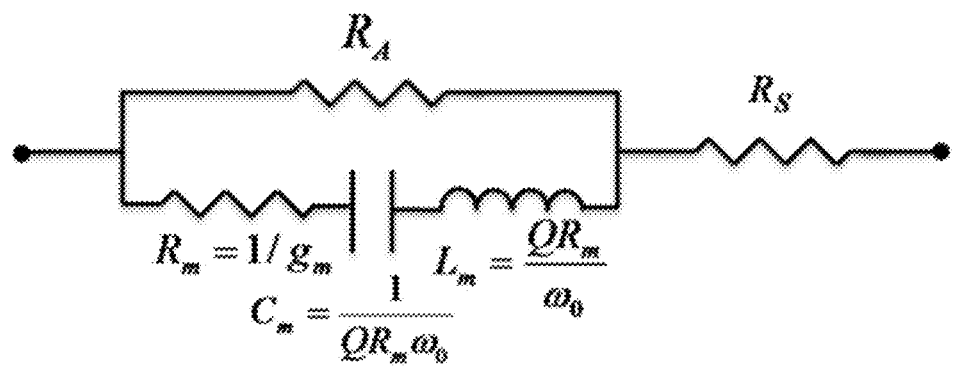
FIG. 2B shows an overall equivalent electrical circuit for a one-port thermally actuated resonator.

FIG. 2A shows a schematic diagram of the three physical domains involved in operation of thermal-piezoresistive resonators according to some embodiments of the invention. The input AC voltage causes a fluctuating thermal changes at block 205, which cause a mechanical force in the actuators at block 210. This can result in mechanical vibrations at resonance frequency modulate the DC current in the actuators due to piezoresistive effect at block 215. FIG. 2B shows an overall equivalent electrical circuit for a one-port thermally actuated resonators with piezoresistive readout. $R_A$ is the electrical resistance of the actuators and $R_S$ is the parasitic resistance of the support beams.

A negative resistance (or negative conductance) is equivalent to an active energy pump. Therefore, thermal piezoresistive resonators can feed some energy back into their mechanical structure rather than just wasting energy through mechanical and/or ohmic losses as passive resonators do. If the absolute value of the negative motional conductance resulting from negative piezoresistive coefficient is increased to reach and surpass the value of $R_A^{-1}$, instead of the resonator losing part of its energy in every cycle, it can gain some extra energy in each cycle. This can lead to instability of the resonant system and self-sustained oscillation.

Figure 3:
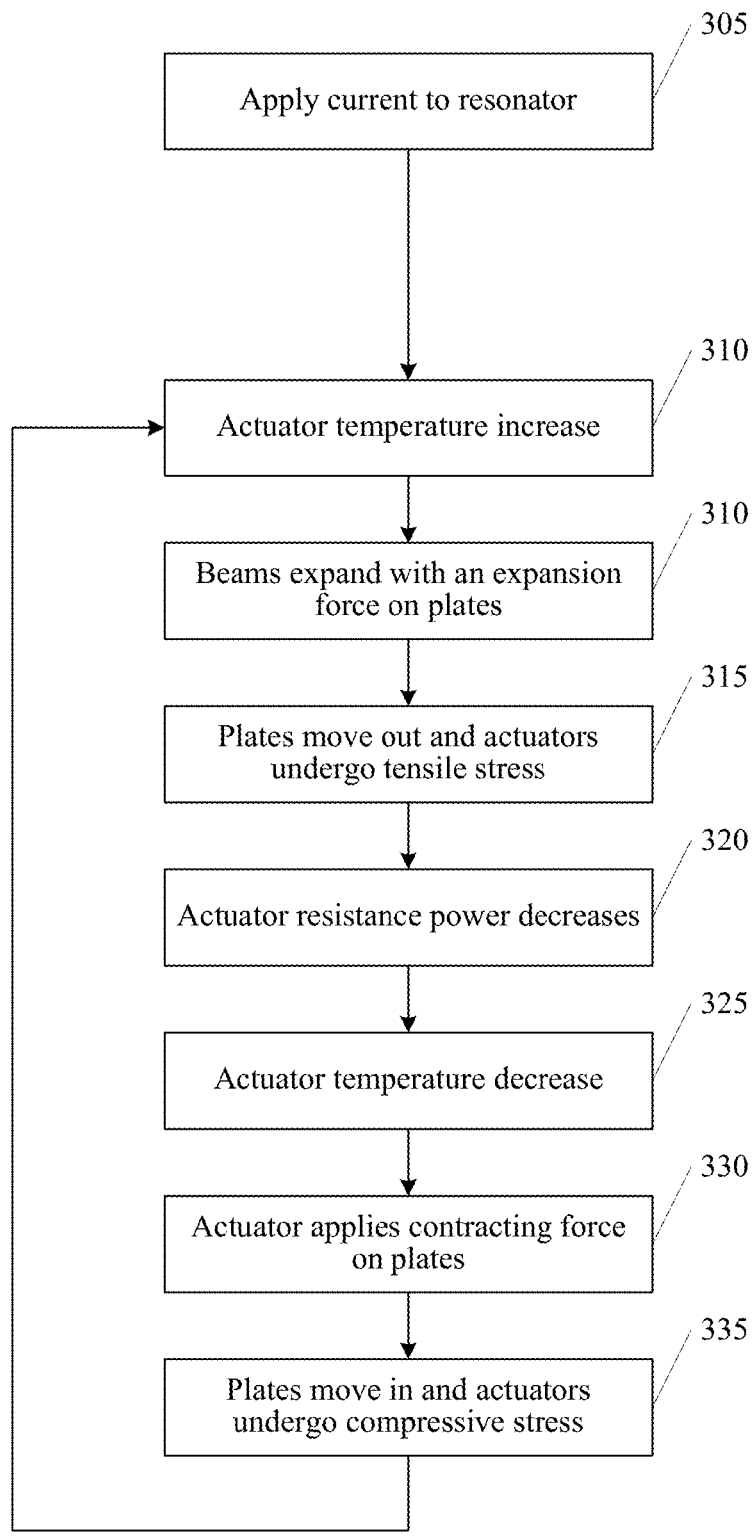
FIG. 3 shows a flowchart of the physical process that occurs within the resonator and according to some embodiments of the invention.

FIG. 3 shows a flowchart 300 of the physical process that occurs within the resonator that causes self-sustained oscillations according to some embodiments of the invention. A constant DC bias voltage can be applied at block 305. This bias voltage can produce a current in beams (e.g., beams 110 and 111) causing the beams to heat up at block 310. The heated beams can then expand at block 315. This expansion can push plates (e.g., plates 105 and 106) further away from each other. Because of the mass (inertia) of the plates, beams can experience an over-expansion after pushing the plates apart. This can results in tensile stress within the beams in block 315. The negative piezoresistive coefficient causes the tensile stress into reduced electrical resistance in the beams at block 320, which can cause a reduction in the temperature of the beam at block 325. This reduction in ohmic power can force the beams to contract at block 330 with possible structural over-contraction. After structural over-contraction (due to the mass of the plates), the beams will be under compressive stress and will have increased electrical resistance at block 335. This again causes the beams to increase in temperature at block 310. If the resulting driving force (due to heating and cooling) in each cycle is large enough to compensate for mechanical losses of the structure, the same sequence is repeated over and over in a self-sustained manner and the vibration amplitude keeps increasing until it is limited by nonlinearities.

As noted above, simple periodic motion can occur by applying a DC bias across the beams. Because of the changes in resistance across the beams, with a constant current the voltage across the beams will vary in response to the changing resistance. Resonance can occur after a number of cycles producing a regular frequency response.

FIG. 4 shows another embodiment of a nano/micromechanical thermal resonator. Resonator 400 includes plate 405 and plate 406 connected together by beam 410 and beam 411. Beams 410 and 411 can be eclectically coupled with pads 425. DC bias current can be applied to beams 410 and 411 through pads 425.

Plates 405 and/or 406 can include a plurality of spacers 450 etched into the body of plates 405 and/or 406. These spacers can be used to control the mass of plates 405 and/or 406. These spacers can also be used to facilitate undercutting during fabrication. Plates 405 and 406 can also be coupled with fixed anchors 430. During oscillation plates 405 and 406 can oscillate relative to anchors 430. In some embodiments, anchors 430 can include gaps 460 and 461 that can aide in motion of plates 405 and 406. These gaps may also allow plates 405 and 406 to more easily vibrate relative to one another. Any number of gaps can be included. Moreover, plates 405 and/or 406 can have any size or shape.

Figure 5:
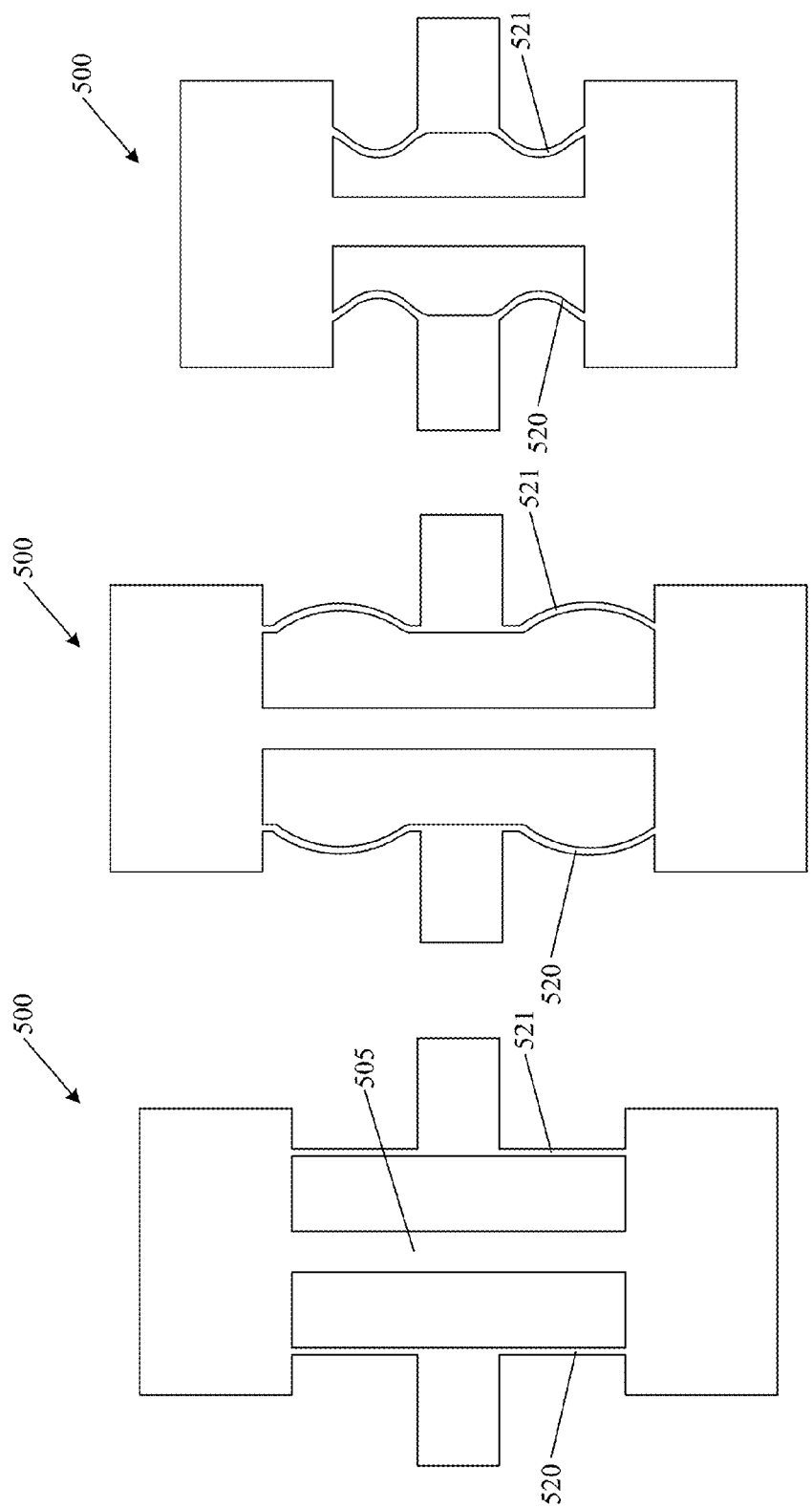
FIG. 5A, 5B, and 5C show another embodiments of a micromechanical resonator in resting, stretched, and compresses states.

FIG. 5A shows another embodiment of a nano/micromechanical thermal resonator. Resonator 500 can include middle beam 505. Middle beam 505 can be wider than beams 520 and 521. In this embodiment, the resulting stiffness of the resonator is mainly determined by the wider middle bar. This can allow for higher resonance frequencies while maintaining very narrow beams 520 and 521. A wider middle beam may compensate for any manufacturing defects or changes in the dimensions of beams 520 and 521. Such defects will have less of an effect on the frequency of the resonator. Such embodiments can effectively decouple frequency variation from manufacturing defects resulting in lower manufacturing tolerances to produce resonators with similar frequency responses.

FIG. 5B shows resonator 500 in a stretched configuration. As shown beams 520 and 521 as well as middle beam 505 are stretched during one portion of the oscillation cycle. FIG. 5C shows resonator 500 in a compressed configuration. As shown beams 520 and 521 as well as middle beam 505 are compressed during another portion of the oscillation cycle. FIG. 5B and 5C show resonator 500 90° out of phase.

Figure 6:
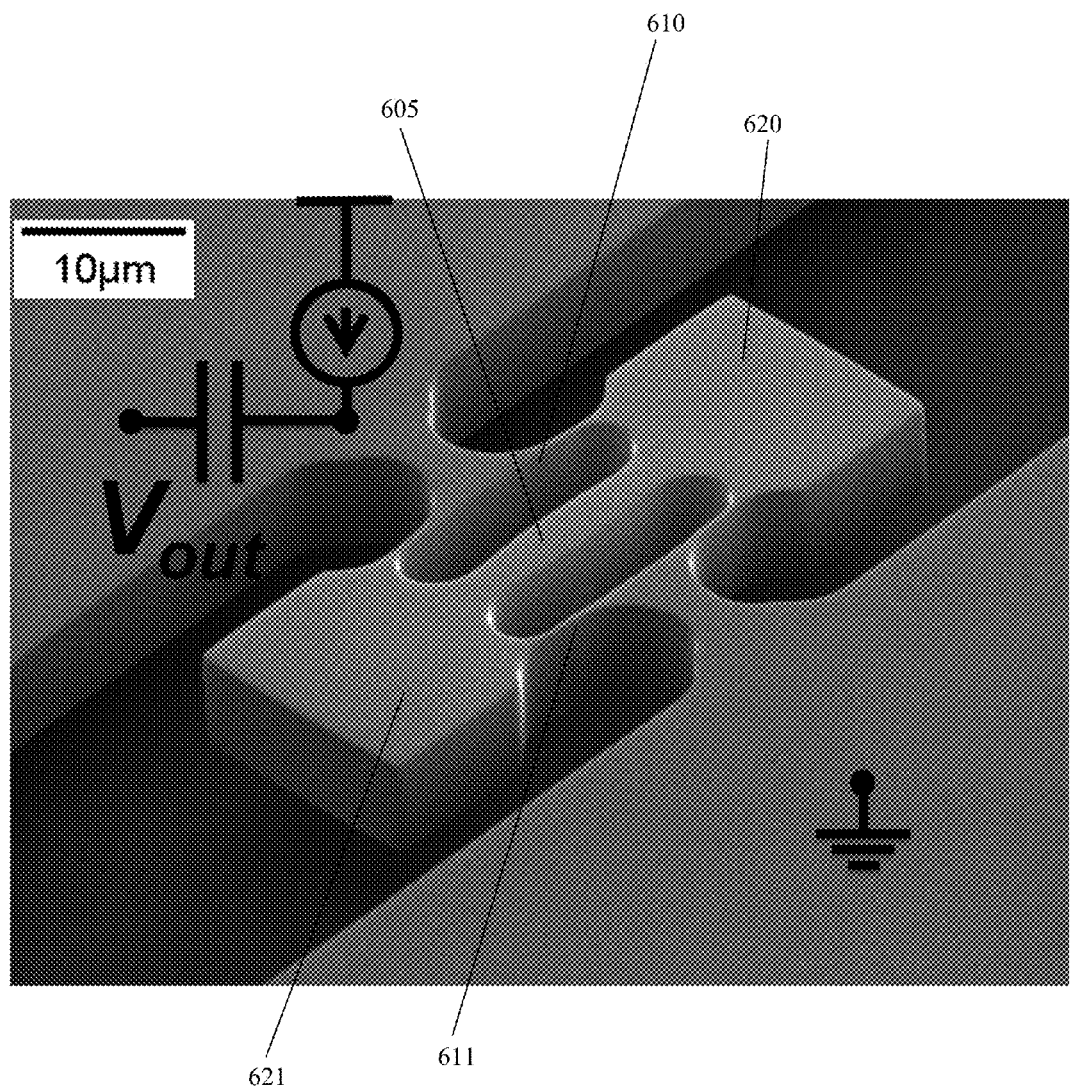
FIG. 6 shows a scanning electron microscope image of a resonator.

FIG. 6 shows a scanning electron microscope image of resonator 600. Resonator 600 includes plates 620 and 621, beams 610 and 611, and middle beam 605. As indicated in the figure, a DC bias current is applied across beams 610 and 611. The voltage across these beams will then vary as the beams thermally expand and compress. In some embodiments, the output voltage may be tied to a decoupling capacitor as indicated.

Resonator 600 was fabricated using the standard single mask SOI-MEMS process on a low resistivity N-type SOI wafer with device layer thickness of 10 µm. Since longitudinal piezoresistive coefficient of silicon reaches its maximum value along the 100 direction, the resonator beams were fabricated along that direction for optimized transduction. Fabrication of resonator 600 included a series of thermal oxidation steps followed by oxide removal in hydrofluoric acid to narrow down the thermal actuators.

Instead of current sources relatively large resistors with values a few times (up to 10×) larger than the electrical resistance of the resonator, can be used to provide the resonator bias currents. By gradually increasing the bias current, after passing a threshold a fixed output frequency can be detected. In some embodiments, the output signal shape can be different than sinusoidal due to existence of different frequency harmonics. In this example, resonator 600 has its first in-plane resonance mode at 17.4 MHz, it can be concluded that the second harmonic is the dominant component. The first harmonic shows itself as uneven level of the consecutive peaks in the output waveform. In addition, the small ups and downs in the waveform can be blamed on higher frequency harmonics. By further increasing the bias current, the output voltage waveform constantly changes and at some point the first frequency harmonic with frequency of ~17.5 MHz becomes dominant.

Rotational Mode Resonators

Figure 7:
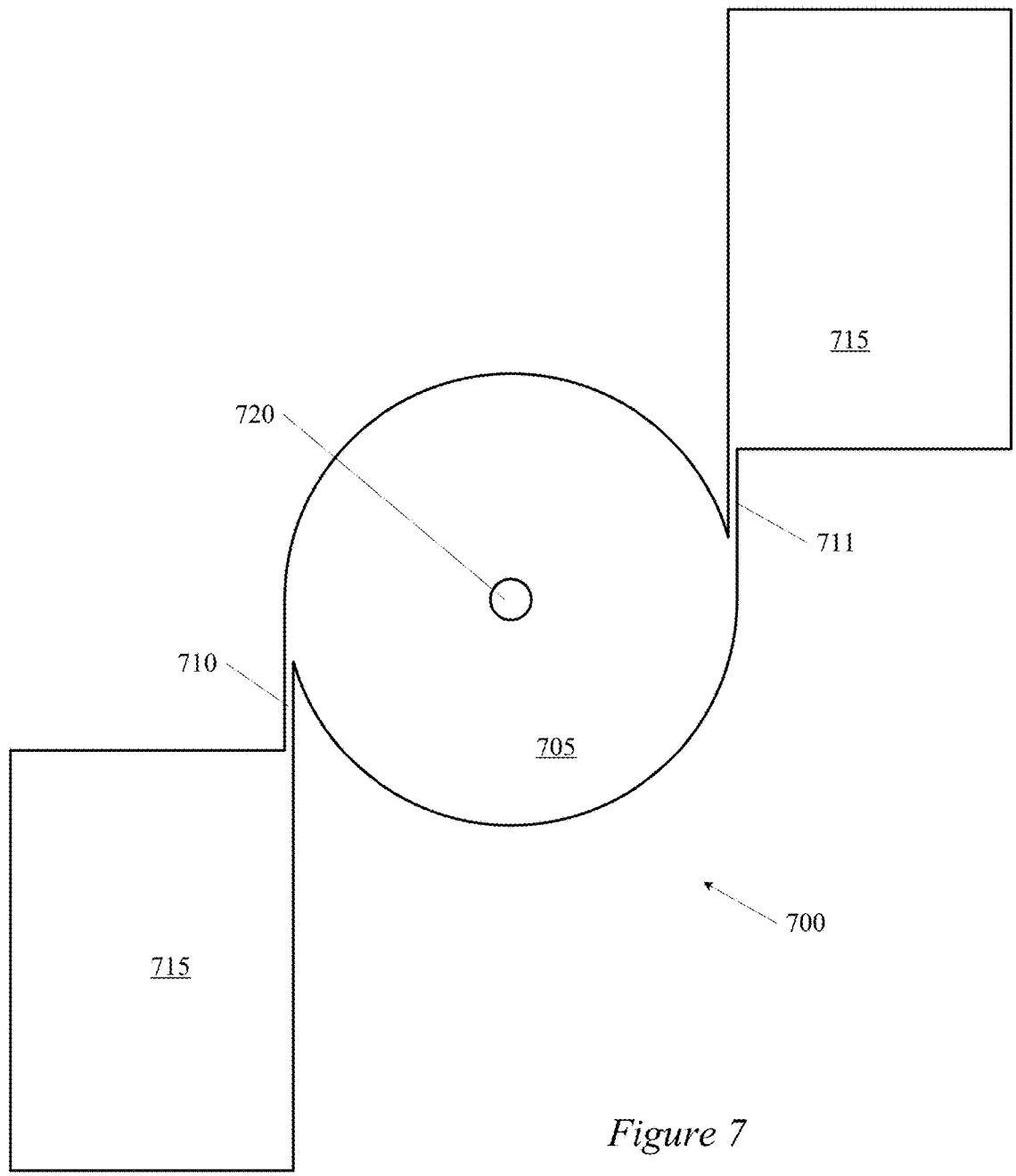
FIG. 7 shows the schematic view of resonator that includes a disk with straight tangential support beams.

FIG. 7 shows a schematic view of resonator 700 that includes disk 705 with straight tangential support beams 710 and 711. Support beams 710 and 711 can act as thermal actuators and/or piezoresistive stress sensors. Thermal actuation can occur by passing a current through beams 710 and 711. This current can be applied to pads 715. In some embodiments, this current can include a combination of a DC current and an AC current, called the actuation current. Disk resonators can be useful for resonance applications in a liquid environment such as in biomedical applications.

In some embodiments, the ohmic power loss in resonator 700 can have a component at the same frequency as the applied AC current: $P_{ac}=2R_e I_{dc} i_{ac}$, where $R_e$ is the electrical resistance between the two pads and $I_{dc}$ and $i_{ac}$ are the applied DC and AC currents respectively. Due to their higher electrical resistance, most of the ohmic loss and therefore heat generation is concentrated in beams 710 and 711. The applied AC power can produce a periodic temperature fluctuations in beams 710 and 711 that can cause alternating stress and strain in the support beams (see e.g., FIG. 3). These stresses and strains can actuate disk 705 in its rotational resonance mode (periodically rotating back and forth around axis 720). As resonator 700 vibrates, the resulting periodic stress changes result in fluctuations in the electrical resistance of the resonator due to the piezoresistive effect. This modulates the DC current passing through the resonator leading to an AC output motional current component that can be used to monitor the resonator vibration amplitude.

While the disk is vibrating in its rotational mode, beams 710 and 711 can vibrate in their extensional mode (periodically elongating and contracting). As a result, all the surfaces of both the disk and its support beams move in parallel to the liquid interface, minimizing the energy loss to the surrounding liquid.

In some embodiments, disk 705 can have a diameter of 500 μm or less. The diameter of disk 705 can also be less than 400 μm, 300 μm, 200 μm, 100 μm, 50 μm, 20 μm, 10 μm, etc. Disk 705 and/or beams 710 and 711, for example, can have a thickness that is less than 100 μm, 80 μm, 60 μm, 40 μm, 20μm, 10 μm, 5 μm, 2 μm, 1, μm, etc. For example, beams 710 and 711 can have width less than 20μm, 10 μm, 5 μm, 4 μm, 2 μm, 1, μm, etc. As another example, beams 710 and 711 can have a length less than 100 μm, 80 μm, 60 μm, 40 μm, 20μm, 10 μm, 5 μm, 2 μm, 1, μm, etc.

Figure 8:
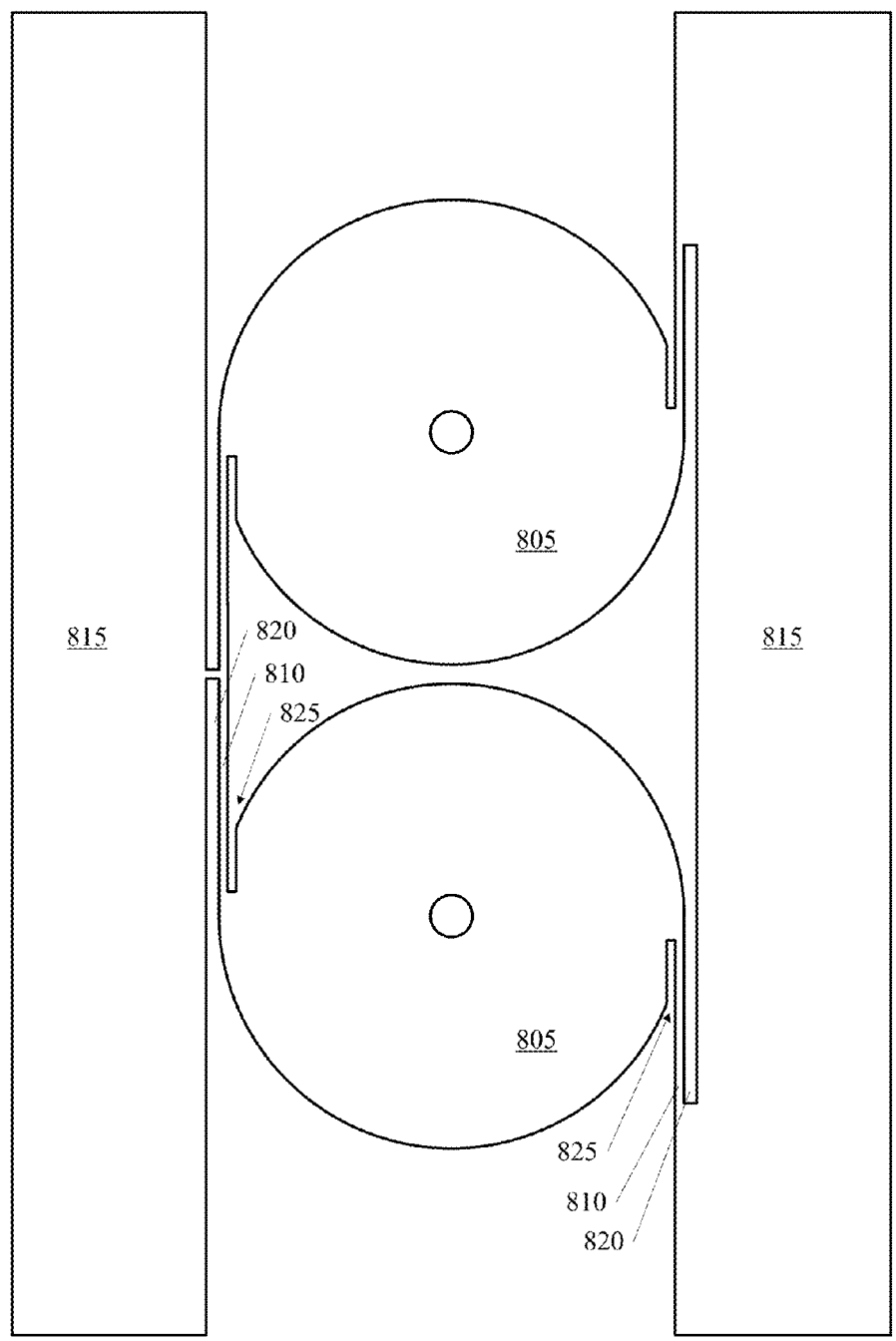
FIG. 8 shows two resonator disks in a parallel configuration.
Figure 9:
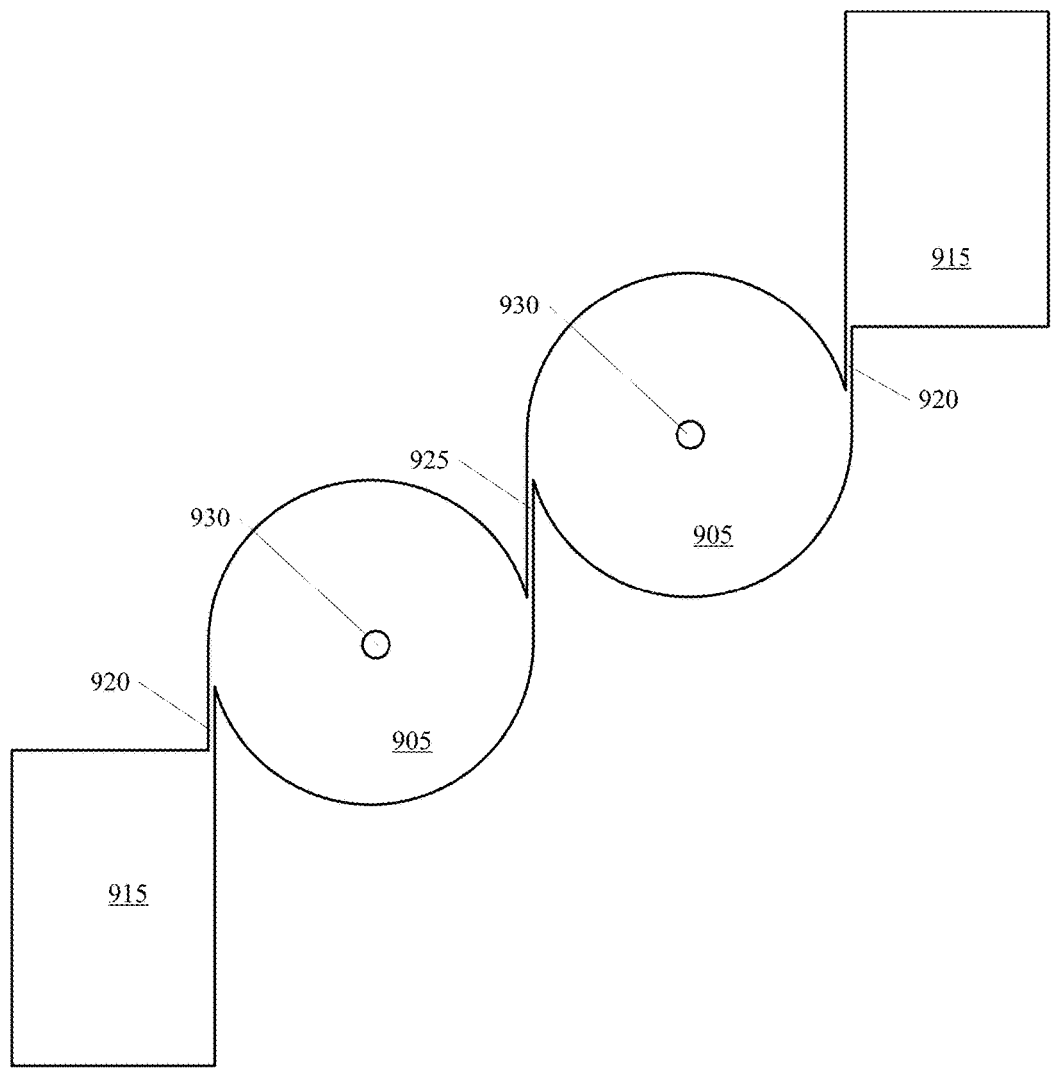
FIG. 9 shows two resonator disks in a series configuration.

Various combinations of disk resonators can also be used. A few examples of such variations and combinations are shown in FIGS. 8 and 9. For example, FIG. 8 shows two resonator disks 805 in a parallel configuration. Resonators 805 includes tangential support beams 810. Support beams 810 are coupled with anchors 815. Tangential support beams 810 can be coupled with resonator disks 805 with gaps 820 and anchors 815 with gap 825. More than two resonator disks 805 can be coupled together in parallel.

FIG. 9 shows two resonator disks in a series configuration. Resonator discs 905 are coupled together via beam 925 and with anchors 915 via beams 920. More than two resonator disks 905 can be coupled together in series. Moreover, multiple resonator disks can be coupled in series and parallel. Holes 930 can be formed in the middle of disk 905 are to aide in the undercut process.

Disk resonators (as well as any other resonators) can be fabricated, for example, using a standard single mask silicon-on-insulator microelectromechanical systems (SOI-MEMS) process. The fabrication process can include silicon deep reactive-ion etching (DRIE) to form the structures out of the silicon device layer, and releasing them by etching an underlying buried oxide (BOX) layer in hydrofluoric acid (HF). Resonators can be fabricated, for example, on a low resistivity N-type substrate with different device layers and/or BOX thicknesses. To optimize resonator electromechanical transduction, the support beams can be aligned to the crystalline direction where the longitudinal piezoresistive coefficients are maximum. Due to the circular shape of holes 930 and the relatively small vibration amplitude in the center of the disks such holes may have negligible effect on viscous damping of the resonator.

Figure 17:
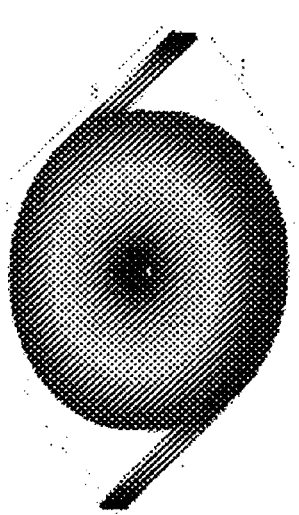
FIG. 17 is a table summarizing measurement results for a resonator having a single disk with straight tangential support beam.
Figure 18:
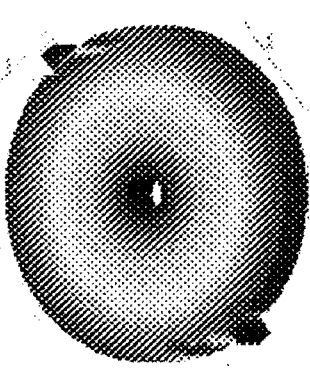
FIG. 18 is a table summarizing measurement results for a resonator having a single disk with rounded support beam.

The tables shown in FIGS.17-19 summarizes measurement results for a variety of different disk resonators of different resonator types with different dimensions in both air and liquid. It also shows the finite element modal analysis for different structures demonstrating the vibration amplitude at different parts of the structure. The modal analysis results show that unlike the other structures the interconnected quad-disks have an off-center rotation which justifies their lower Q in liquid despite their relatively high Q in Air.

In the tables shown in FIGS. 17-19 , "D" represents the diameter of the disk, "L" is the length of the beams and "H" is the thickness of the resonator. The tables shown in FIGS. 17-19 shows results for resonators in both air and heptane. The resonators tested typically have relatively low quality factors in air (due to excessive support loss). However, an unprecedented quality factor of 304 was measured in heptane. Such high Q values in heptane can be attributed to the elimination of the stroking surfaces from the mode shape.

Disk resonators can also be used in aqueous solutions. As such, disk resonators can be used, for example, in biotechnology applications.

Figure 14:
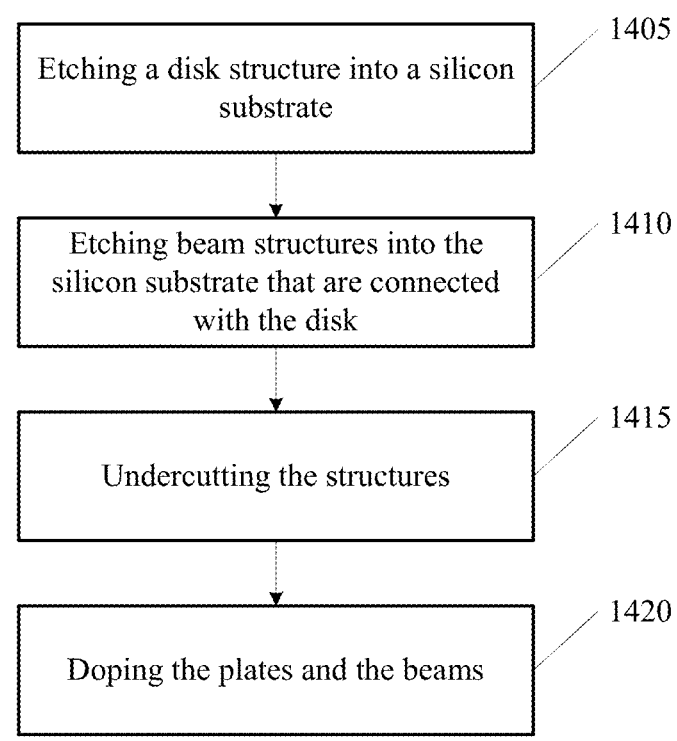
FIG. 14 is a flowchart of a process for fabricating a disk resonator according to some embodiments of the invention.

FIG. 14 shows a flowchart of a process for fabricating a disk resonator according to some embodiments of the invention. At block 1405 and 1410 the disk and the beams are etched into the substrate. These can be etched in separate steps or in the same step. Anchors 430 (e.g., anchors 715) can also be etched into the substrate. Any number of etching or lithography techniques can be used to form the parts of the resonator. For example, wet chemical etching, dry etching, masking, deep reactive ion etching, photolithography, CMOS fabrication processes, etc. techniques can be used At block 1415 the disk and beams can be suspended on top of the substrate using undercutting techniques. Once etched and possible undercut, the disk and beams may undergo various post processing steps such as annealing, doping, and/or baking These post processing steps may occur before or after undercutting. In some embodiments, the disk and beams may be doped with dopants at block 1420. This doping may occur at any time during the process and may not occur at all.

Applications of Resonators

Frequency Reference Embodiments

Embodiments of the invention can be used in a number of applications. Some embodiments of the invention can be used as a timing reference in an electronic application. For example, resonators can be fabricated on-chip with the logic and/or memory. A plurality of resonators can be etched into the silicon on the chip and used by the chip as a frequency reference.

Particle Mass Sensor Embodiments

Figure 10:
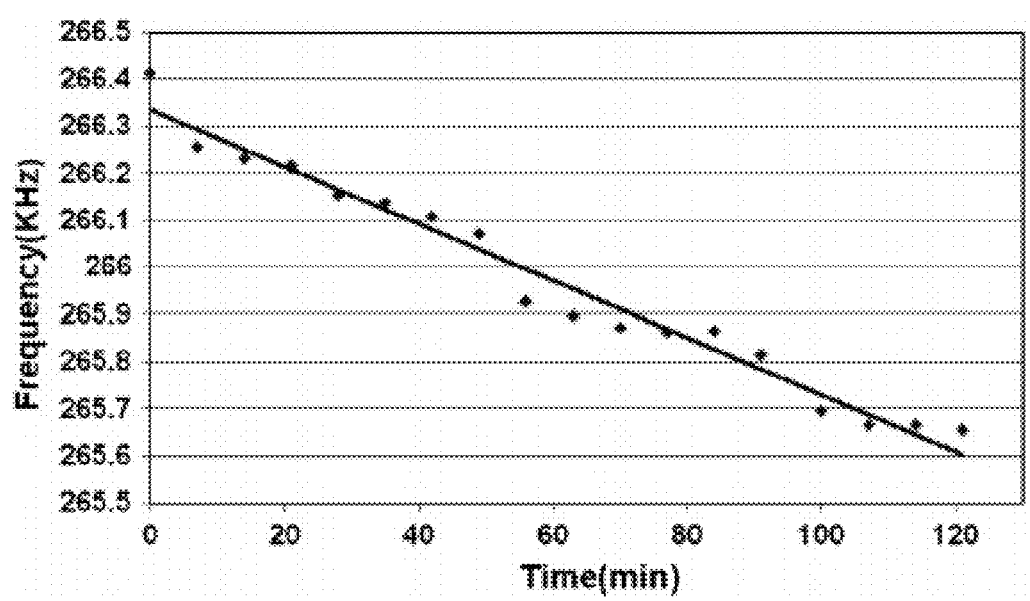
FIG. 10 is a graph showing the frequency response of a resonator to deposited particles using embodiments of the invention.

Embodiments of the invention can also be used as a particle mass sensor. The frequency response of any of the resonators described in the various embodiments of the invention can be inversely proportional to the square root of the mass of the resonator. As such, the frequency will change as the mass of the resonator changes. Because of this relationship, the frequency response will change as particles buildup on the mass of the resonators. FIG. 10 shows a graph of frequency measurements over time. As particles buildup on the masses of the resonators, the frequency of the resonator decreases in discrete steps.

Figure 11:
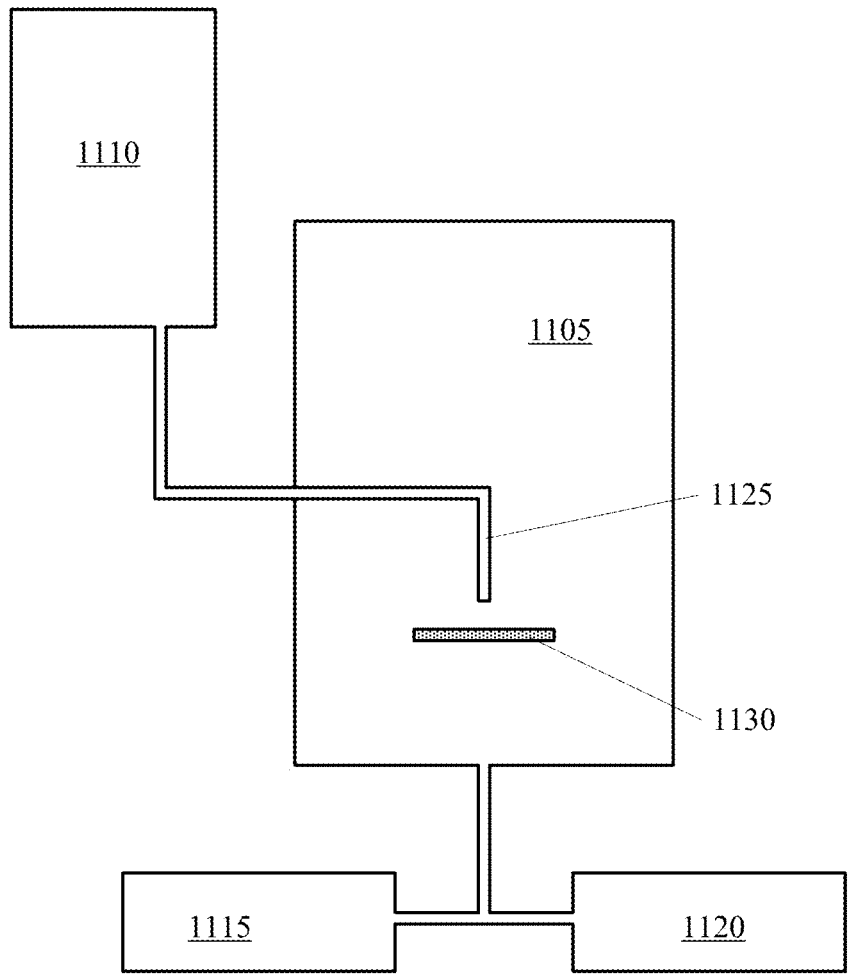
FIG. 11 is diagram of a particle mass sensor according to some embodiments of the invention.

FIG. 11 shows an embodiment of a particle mass sensor according to some embodiments of the invention. Chamber 1105 can house mass sensor substrate 1130 comprising one or more resonators positioned below particle nozzle 1125. Nozzle 1125 can be placed, for example, around 1 mm from substrate 1130. Pump 1120 can be used to maintain a low pressure within chamber 1105 and pressure sensor 1115 can measure the pressure within chamber 1105. Particles from particle source 1110 can be sucked onto sensor 1130 due to low pressure in the chamber. When actuation voltages or currents are applied to mass sensor 1130, the frequency of the micromechanical resonator can be measured. The mass of particles deposited on sensor 1130 can be determined in real time by measuring the resulting change in frequency.

Figure 12:
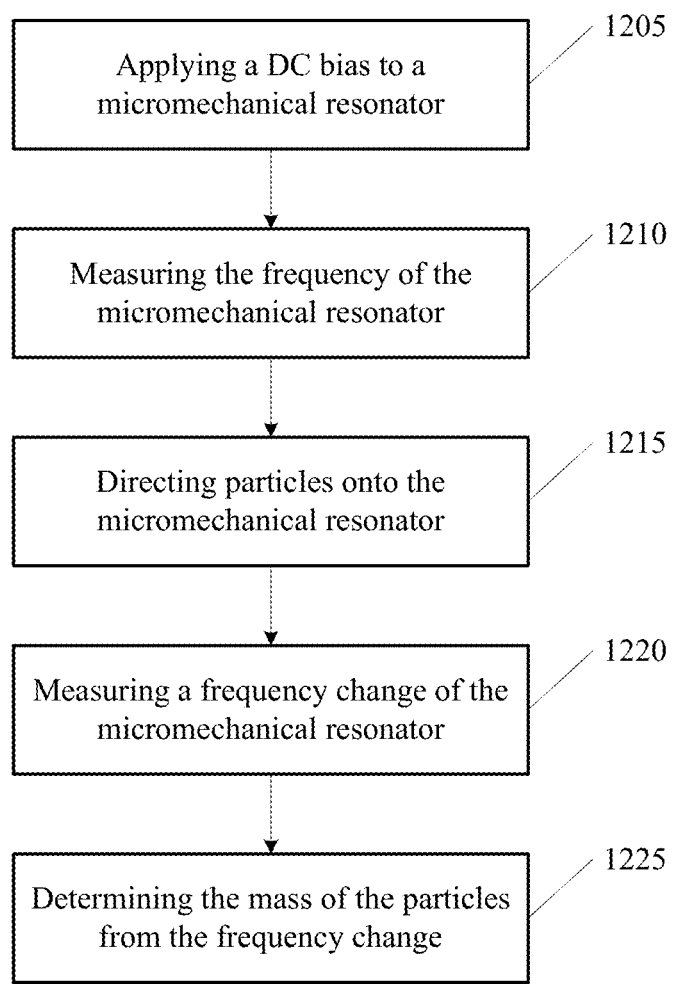
FIG. 12 is a flowchart of a process for sensing the mass of particles according to some embodiments of the invention.

FIG. 12 is a flowchart of a process for sensing the mass of particles according to some embodiments of the invention. At block 1205 a DC bias current is applied to micromechanical resonator. The resonator can be any of the resonators described herein or any other micromechanical resonator known in the art. In some situations, the resonator may need some time to stabilize and/or come to resonance. At block 1210 the frequency of the resonator can be measured. This frequency can be noted as the baseline frequency.

At block 1215 particles can be directed on to the resonator. These particles can be directed onto the resonator, for example, through nozzle 1025. In some embodiments, the particles can be in a pressurized vessel and directed toward the resonator under pressure. As the particles land on, adhere, rest, stick, etc. to the resonator, the mass of the plates change causing a change in the frequency response. This frequency can be measured at block 1120. The mass of the particles can be determined at block 1125.

Viscosity Sensor

Some embodiments of the invention can be used as a viscosity sensor. For example, the frequency response from a disk resonant can vary based on the viscosity of the fluid or liquid within which the resonator is placed. Thus, changes in viscosity can be determined by measuring the frequency response of the resonator.

Analyte Sensor

In some embodiments, a disk resonator can be used within a liquid environment to sense the presence of an analyte. This can occur by allowing the analyte of interest to couple (e.g., adhere, absorb, bond) with the surface of the disk. The disk can be coated with a material, (e.g., a polymer) that selectively adheres, couples with, or absorbs a particle or molecule of interest. The frequency of the resonator can be monitored over time. Coupling (e.g. adherence or bonding) of the molecule of interest can be determined by noting a resulting frequency change in the resonator.

For example, a disk resonator can be used to measure the presence of octadecylamine molecules (an amine molecule with a straight chain of 18 carbon atoms) in an aqueous solution.

In order for the disk to couple (e.g., absorb, bond, adhere) with octadecylamine molecules intermediate molecules containing epoxide groups are to be attached to the disk. These intermediate molecules can be applied as a film to the disk. This can be done, for example, by activating the disk surface by oxidation in 1N $HNO_3$ for 30-60 min followed by a rinse in DI water, acetone, and ethanol for 5 min each. In order to attach the epoxide groups to the silicon surface, the disk was soaked for 5 hours at 80~ in a solution consisting of 24 parts xylene, 8 parts 3-glycidoxypropyltrimethoxysilane and 1 part N,N-diisopropylethylamine. Excess reagents were can be removed by three washes in acetone and/or ether. The first frequency measurement was performed in this step after drying the resonators.

After measuring and recording the resonator resonance frequencies with different bias currents, octadecylamine attachment was performed by immersing the resonator in a 5 mM solution of octadecylamine in ethanol for a period of time. The excess reagents on the resonator were rinsed off in methanol and ether. The measured frequencies before and after octadecylamine attachment will show a clear and consistent frequency shift.

During the surface fictionalization, each crystal with a lattice constant of 5.43Ao consists of eight open bonds on 100 silicon surface exposed to reaction reagents. Attachment of each epoxide group requires linking to three silicon atoms on the surface. This means that if all the available bonds are used for linking with 100% packing, 8.8 epoxide groups will be available in every $nm^2$ of silicon surface.

On the other hand, according to the device mass, reference frequency value and frequency shift after octadecylamine attachment, the added mass for the 1st measured resonator with the resonance frequency of 30.4 MHz is:

$$\frac{\Delta f}{f} = -\frac{\Delta m}{m}.$$

Noting that $\Delta m=1.0$ pg. Therefore, considering octadecylamine molecular weight, the added 1.0 pg of octadecylamine is equal to $2.2 \times 10^9$ added molecules on the on the surface. Based on the resonator surface area of $3.6 \times 10^{-9} m^2$, we will end up having 0.61 molecules in every $nm^2$, which is equivalent to 6.93% of the calculated theoretical limit of the added molecules in 1 $nm^2$.

The above chemistries can also be use, for example, to sense amino terminated DNA single strands. Various other films or substances can be applied to the disk that can adhere, absorb, or couple with specific molecules or molecule types. Thus, embodiments of the invention can be used as a molecular probe for detection of complimentary target molecules.

Any molecular pairs with high affinity towards each other can be used. This can include a film or coating where molecules are covalently bonded to the resonator surface, or embedded within a physically absorbed polymer layer and the other molecule is the analyte in the solution. For example, Antigen-Antibodies can be used to coat a sensor. Then the weight or presence of a complementary single strand DNA can be determined.

Temperature Compensation

Silicon can become softer as temperatures rise and stiffer as temperatures lower. Changes in stiffness resulting from temperature can change the frequency of the resonator. This temperature drift of frequency can be as much as −40 ppm/° C. Because the actuator beams used in the resonators described herein are made from silicon, the softening and/or stiffening of silicon can affect the frequency of the resonator. To reduce the frequency's temperature dependency, the silicon can be doped with various dopants. For example, the silicon can be doped with boron, creating p-type silicon, or doped with phosphorus, creating n-type silicon. These dopants can be added before or after resonator fabrication. Other types of dopants may also be used. These may include, for example, germanium, arsenic, antimony, aluminum, gallium, etc. In some embodiments, group 3 or group 5 elements.

In some embodiments, the DC bias current can be adjusted to compensate for the temperature drift. For example, raising the bias current can lead to a more positive temperature drift coefficient and lowering the bias current can lead to a more negative temperature drift coefficient. In some embodiments, the resonators can be both doped and use current compensation to correct for temperature drift. Thus, a resonator fabricated from doped materials can have a substantially lower temperature drift. In some cases, a doped resonator can have a drift that is near zero (e.g., between 2 ppm/° C. and −2 ppm/° C.). A small adjustment to the DC bias can move the drift nearer to or to zero (e.g., changing the current from 1.3 mA to 1.33 mA). Thus a combination of doped materials and DC bias adjustments can compensate for temperature drift.

Figure 15:
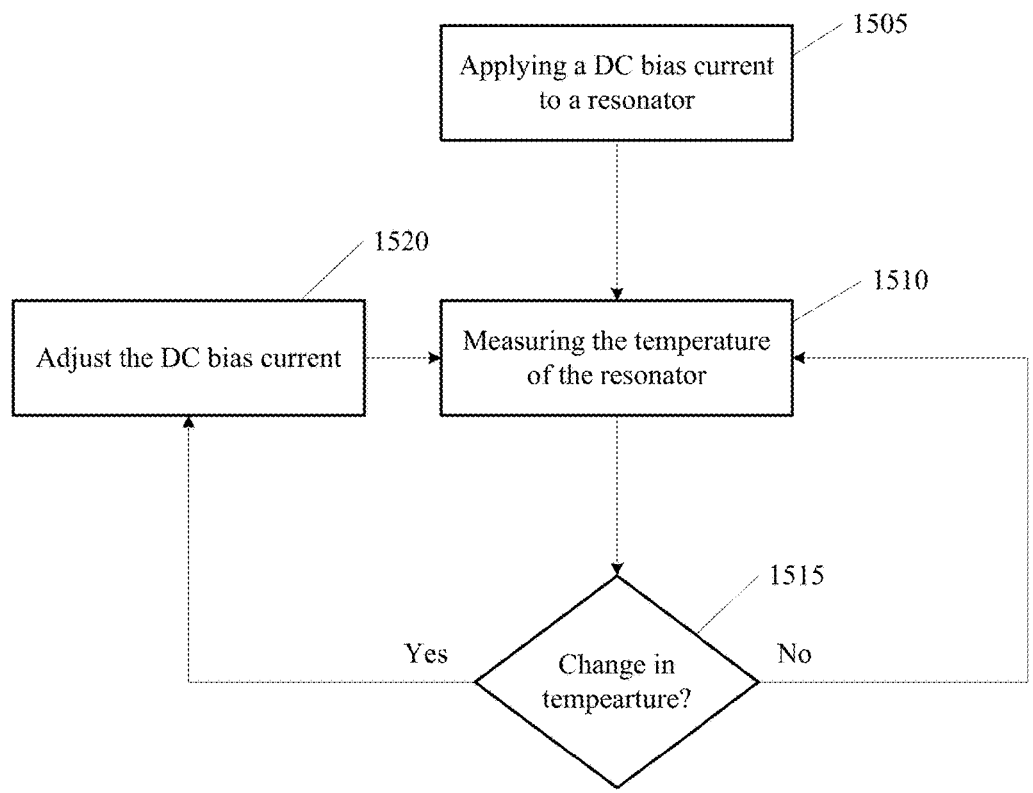
FIG. 15 is a flowchart of a process for compensating for temperature drift according to some embodiments of the invention.

Temperature compensation can also occur in an active manner. FIG. 15 shows a flowchart of a process to perform active frequency compensation according to some embodiments of the invention. At block 1505 a DC bias current is applied to a resonator. In some situations, like disk resonators, an AC bias current may also be applied. The temperature of the resonator can be measured at block 1510. At block 1515, the process can determine if a frequency drift is occurring by monitoring the temperature over time. Because temperature and frequency are related, a noted change of temperature signifies a change in frequency. If there is temperature change then the process simply repeats by returning to block 1510. If the temperature is changing, as determined at block 1515, then the DC bias current can be adjusted at block 1520. If the temperature change is positive then the bias current can be increased. If the temperature change is negative then the bias current can be decreased.

The following table summarizes measured TCF values for a number of different test resonators. The trend observed in all the doped resonators is that when operated at higher bias currents (higher static temperature) the TCF values become more positive (or less negative). This could be explained by the elevated temperature having a similar effect on the band structure of silicon as degenerate doping. By having the right doping level and bias current, potentially zero TCF can be achieved for such devices.

In the following table "a" represents is the width of the plates and "b" is the length of the plates. "H" represents the thickness of the resonator, "L" the length of the beams, and "W" the width of the beams.

described in conjunction with FIGS. 12-15. Computer system 1600, for example, can be used to compute particle mass values from frequency measurements and/or temperature drift changes from frequency values. The drawing illustrates how individual system elements can be implemented in a separated or more integrated manner. The computer 1600 is shown having hardware elements that are electrically coupled via bus 1626. Network interface 1652 can communicatively couple the computational device 1600 with another computer, for example, through a network such as the Internet. The hardware elements can include a processor 1602, an input device 1604, an output device 1606, a storage device 1608, a computer-readable storage media reader 1610a, a communications system 1614, a processing acceleration unit 1616 such as a DSP or special-purpose processor, and memory 1618. The computer-readable storage media reader 1610a can be further connected to a computer-readable storage medium 1610b, the combination comprehensively representing remote, local, fixed, and/or removable storage devices plus storage media for temporarily and/or more permanently containing computer-readable information.

Resonator interface 1650 is coupled with bus 1626. In some embodiments, resonator interface 1650 can be any type of communication interface. For example, resonator interface 1650 can be a USB interface, UART interface, serial interface, parallel interface, etc. Resonator interface 1650 can be configured to couple directly with any type of resonator system or particle mass sensing system.

The computer system 1600 also comprises software elements, shown as being currently located within working memory 1620, including an operating system 1624 and other code 1622, such as a program designed to implement methods and/or processes described herein. In some embodiments, other code 1622 can include software that provides instructions for the various processes described herein. In some embodiments, other code 1622 can include software that can perform the various functions or processes described herein. It will be apparent to those skilled in the art that substantial variations can be used in accordance with specific requirements. For example, customized hardware might also be used and/or particular elements might be implemented in hardware, software (including portable soft-

| Resonator Dimensions (μm) | | | | | Actuator Tilt | Freq. | | Bias Current | $R_{DC}$ | $g_m$ | Power | Phos. Dope @ | Annealed @ 1100° C. | TCF |
|---|---|---|---|---|---|---|---|---|---|---|---|---|---|---|
| A | b | L | W | H | Angle | (MHz) | $Q_{air}$ | (mA) | (Ω) | (μS) | (mW) | 950° C. | (hours) | PPM/° C. |
| 200 | 200 | 20 | 4 | 5 | 45 | 3.78 | 4800 | 45.3 | 11.5 | −29.5 | 23.5 | 2 hours | 7 | 1.13 |
| | | | | | | | 3900 | 59.5 | 11.5 | −52.6 | 40.7 | | | 1.18 |
| 100 | 100 | 6 | 2 | 5 | 0 | 6.59 | 9000 | 34.4 | 10 | −78.4 | 11.8 | | | 0.32 |
| | | | | | | | 11000 | 52.1 | 10 | −167 | 27.1 | | | 0.79 |
| 30.2 | 20.2 | 30.8 | 0.2 | 2.2 | 15 | 8.21 | 7500 | 1.07 | 155 | — | 0.18 | | 2.5 | −0.54 |
| | | | | | | | 7000 | 1.30 | 155 | — | 0.26 | | | −0.05 |
| 30.6 | 20.6 | 14.9 | 0.6 | 2.6 | 0 | 23.2 | 2550 | 5.31 | 50.5 | −175 | 1.42 | | | 0.67 |
| 15 | 10 | 11.7 | 0.8 | 3.5 | 0 | 60.6 | 490 | 12.5 | 46.5 | −260 | 7.29 | | | −2.4 |
| | | | | | | | 59.2 | 395 | 17.1 | 46.5 | −510 | 13.6 | | | −1.8 |

Computer System

Figure 16:
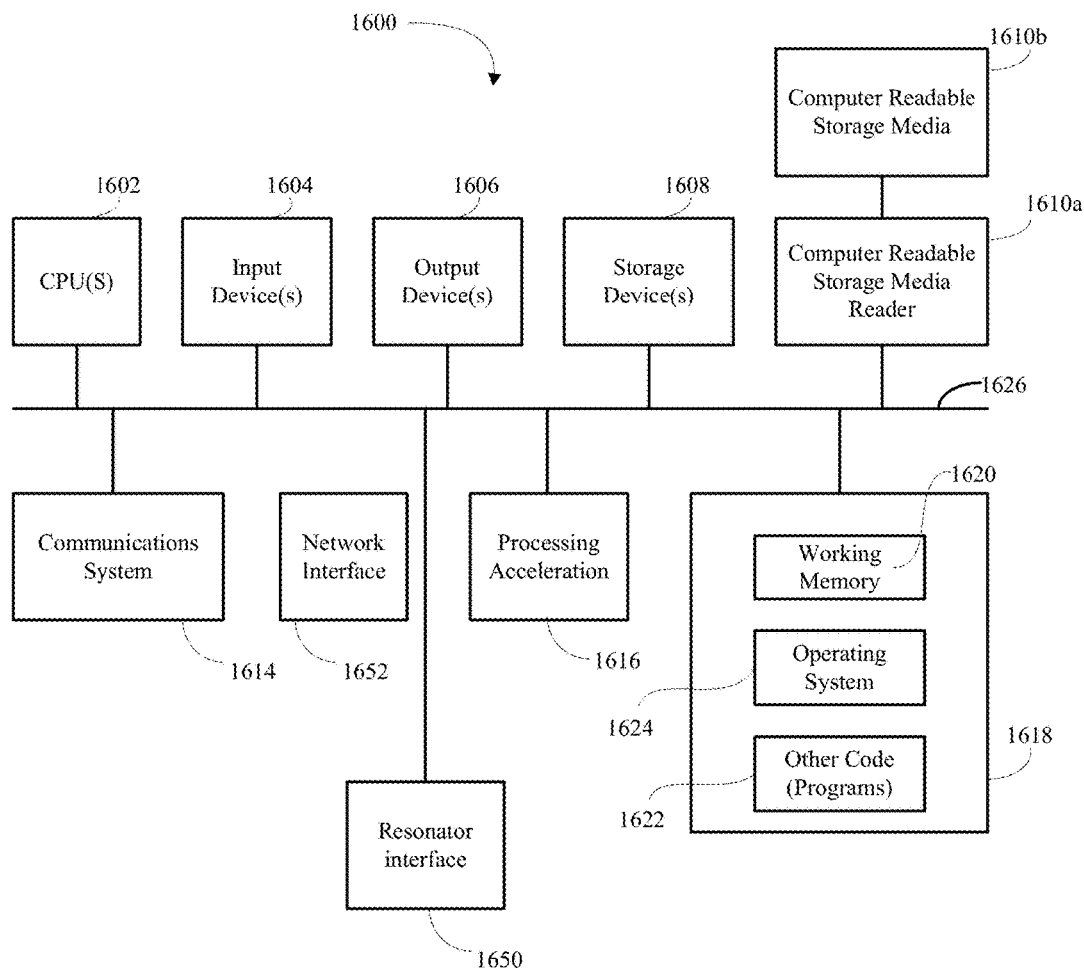
FIG. 16 shows a simplified block diagram of a computational system that can be used to implement embodiments of the invention.

FIG. 16 shows a simplified block diagram of a computer system 1600 that can be coupled with a resonator and/or a sensor for computation purposes according to embodiments of the invention. Computer system 1600 can be used, for example, to perform any or all the computations shown in or ware, such as applets), or both. Further, connection to other computing devices such as network input/output devices can be employed.

The foregoing is provided for purposes of illustrating, explaining, and describing embodiments of the present invention. Further modifications and adaptations to these embodiments will be apparent to those skilled in the art and may be made without departing from the scope or spirit of the invention. Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A micromechanical resonator comprising:
   a substrate;
   a first plate disposed on the substrate and not coupled with the substrate;
   a first anchor coupled to the first plate and coupled with the substrate;
   a second plate disposed on the substrate and not coupled with the substrate;
   a second anchor coupled to the second plate and the substrate;
   a first beam coupled with the first plate and the second plate;
   a second beam coupled with the first plate and the second plate; and
   a first pad coupled with the first beam;
   a second pad coupled with the second beam,
   wherein the first pad and the second pad are configured to apply a DC current to the first beam and the second beam that flows from the first pad to the second pad through the first beam and second beam, and at least one of the first plate and the second plate,
   wherein the two plates resonate in response to flux in thermal energy when the DC current is applied to the first beam and second beam,
   wherein a voltage across the first beam and/or the second beam varies in response to the DC current applied to the first beam and second beam, wherein the first plate and the second plate have the same mass within fabrication tolerances.

2. The micromechanical resonator according to claim 1, wherein the first plate or the second plate have one dimension less than or equal to 10 μm.

3. The micromechanical resonator according to claim 1, wherein the first plate and the second plate comprise silicon.

4. The micromechanical resonator according to claim 1, wherein the first plate and the second plate comprise doped silicon.

5. The micromechanical resonator according to claim 1, wherein the first plate, the second plate, the first beam, and the second beam comprise a unitary structure.

6. The micromechanical resonator according to claim 1, wherein the DC current flows from the first pad to the first beam, then to one or more of the first plate and the second plate, then to the second beam, and then to the second pad.

7. The micromechanical resonator according to claim 1, wherein the first beam is substantially parallel to the second beam.

8. The micromechanical resonator according to claim 1, wherein the first beam and the second beam are electrically and physically coupled only by the first plate and the second plate.

9. The micromechanical resonator according to claim 1, wherein the first pad is directly physically coupled to an approximate middle of the first beam, wherein the first beam flexes under tensile and compressive stresses resulting from the DC current.

10. The micromechanical resonator according to claim 1, wherein the first plate, the second plate, the first beam, the second beam, the first pad, and the second pad each has a single top surface, all the top surfaces being substantially coplanar.

11. The micromechanical resonator according to claim 1, further comprising a third beam, wherein the third beam is coupled between the first plate and the second plate and is positioned between the first beam and the second beam.

12. A method comprising:
    etching a first plate and a second plate within a substrate, wherein each of the first plate and the second plate has one dimension less than or equal to 500 μm;
    etching a first beam within the substrate, the first beam connected with the first plate and the second plate, wherein the first plate, the second plate, and the first beam each has a single top surface, all the top surfaces etched to be substantially coplanar;
    etching a second beam within the substrate, the second beam connected with the first plate and the second plate, wherein the first plate, the second plate, and the second beam each has a single top surface, all the top surfaces etched to be substantially coplanar;
    etching a first anchor and a second anchor within the substrate; and
    undercutting the first beam, the second beam, the first plate and the second plate;
    wherein the first anchor and the second anchor are coupled with the substrate.

13. The method according to claim 12, wherein the first plate, the second plate, the first beam, and the second beam are etched as a unitary structure.

14. The method according to claim 12, wherein the first plate and/or the second plate has one dimension less than or equal to 50 μm.

15. A micromechanical resonator, comprising:
    a substrate;
    a first anchor coupled with the substrate;
    a first plate undercut from the substrate and coupled with the first anchor;
    a second anchor coupled with the substrate;
    a second plate undercut from the substrate and coupled with the substrate;
    a first beam coupled with the first plate and the second plate;
    a second beam coupled with the first plate and the second plate; and
    two pads electrically coupled with the first beam and the second beam, and configured to apply a DC current to the first beam and the second beam such that the first plate and second plate resonate in response to flux in thermal energy when the DC current runs through the first beam and the second beam,
    wherein the first plate, the second plate, the first beam and the second beam, and the two pads each has a single top surface, all the top surfaces being substantially wherein the first plate and the second plate have the same mass within fabrication tolerances.

16. The micromechanical resonator according to claim 15, wherein the first beam and the second beam are electrically and physically coupled only by the first plate and the second plate.

17. The micromechanical resonator according to claim 15, wherein DC current flows from a first pad of the two pads to the first beam, then to one or more of the first plate and second plate, then to the second beam, and then to a second pad of the two pads.

18. The micromechanical resonator according to claim 15, further comprising a third beam coupled between the first plate and the second plate and positioned between the first beam and the second beam.

* * * * *